United States Patent [19]

Navratil

[11] Patent Number: 5,375,614
[45] Date of Patent: Dec. 27, 1994

[54] DENTAL FLOSS

[76] Inventor: Zdenek Navratil, Gassackerstrasse 32, 3033 Wohlen, Switzerland

[21] Appl. No.: 78,206

[22] Filed: Jun. 25, 1993

[30] Foreign Application Priority Data

Oct. 29, 1991 [CH] Switzerland .................... 3161/91-9
Oct. 20, 1992 [WO] WIPO ................ PCT/CH92/00213

[51] Int. Cl.⁵ ............................................. A61C 15/00
[52] U.S. Cl. .................................... 132/325; 132/326
[58] Field of Search ............... 132/323, 324, 325, 326, 132/327

[56] References Cited

U.S. PATENT DOCUMENTS

| | | | |
|---|---|---|---|
| 924,543 | 6/1909 | Dysant | 132/324 |
| 3,340,881 | 9/1967 | Cowan | 132/325 |
| 3,759,273 | 9/1973 | Kraus | 132/92 R |
| 3,924,647 | 12/1975 | Lindblad | 132/92 R |
| 4,790,336 | 12/1988 | Kuo | 132/325 |
| 5,038,806 | 8/1991 | Ewald | 132/325 |
| 5,085,236 | 2/1992 | Odneal et al. | 132/324 X |

FOREIGN PATENT DOCUMENTS 1359802 7/1974 United Kingdom .
9107143 5/1991 WIPO .

Primary Examiner—Gene Mancene
Assistant Examiner—Nicholas D. Lucchesi

[57] ABSTRACT

A dental flosser (10) has a handle (36) with a pair of ends. On one end of the handle is a fork (13) with a pair of teeth (14, 16). On the other end of the handle is a floss reservoir (38) with a spool of dental floss (48) and a centrally disposed spindle (40) mounted therein. A reeling spool (42) is rotatably mounted on the spindle (40) and secured with a screw (41) on the spindle (40). The floss is extended from the floss reservoir (38), through a groove (54) between cross groove (57) and lock device (45), through the groove (20) of the handle (36), through the space between the teeth (14, 16) of the fork (13), through the groove (22) of the handle (36) and is wound on the reeling spool (42). One of the projections (60) engages lock device (45), when the reeling spool (42) is rotated to a locking position, to bias lock device (45) downwardly, thereby clamping a length of floss. The other projection (62) engages locking tooth (64) and stop tooth (66), thereby securing the reeling spool against reverse rotation. To provide a fresh supply of floss between the teeth (24,26) of the fork (13), the reeling spool (42) has to be rotated clockwise by 180°.

11 Claims, 2 Drawing Sheets

U.S. Patent  Dec. 27, 1994  Sheet 1 of 2  5,375,614
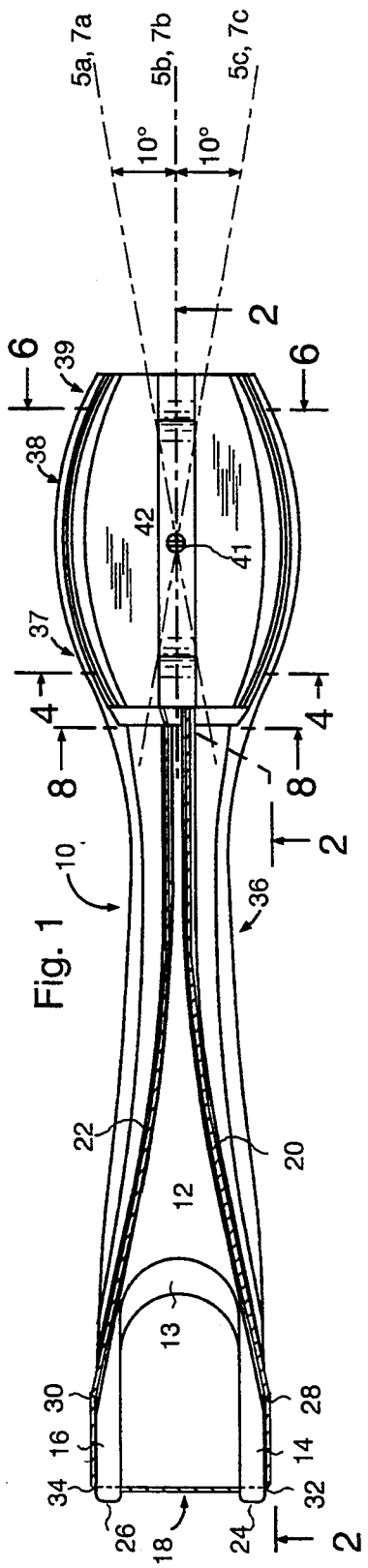
Fig. 1
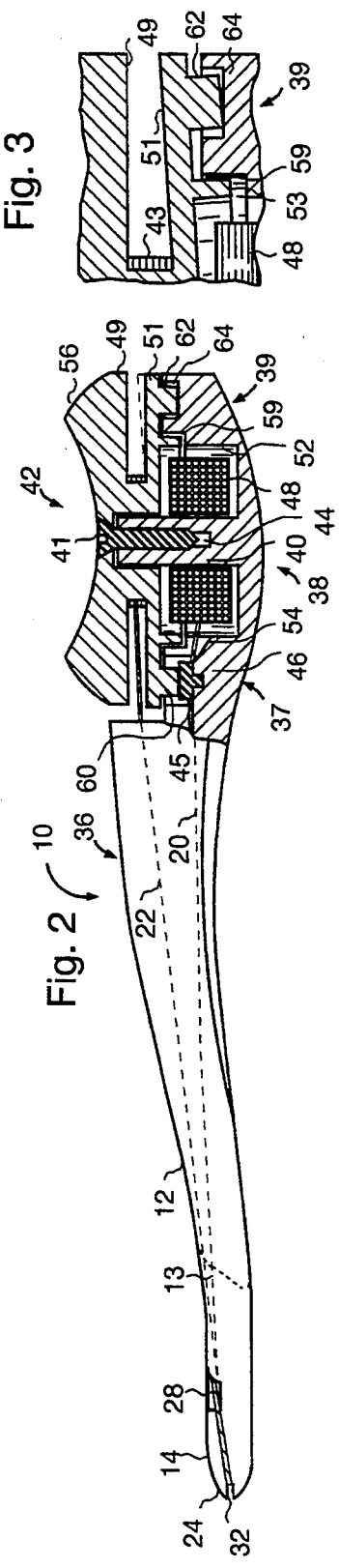
Fig. 2
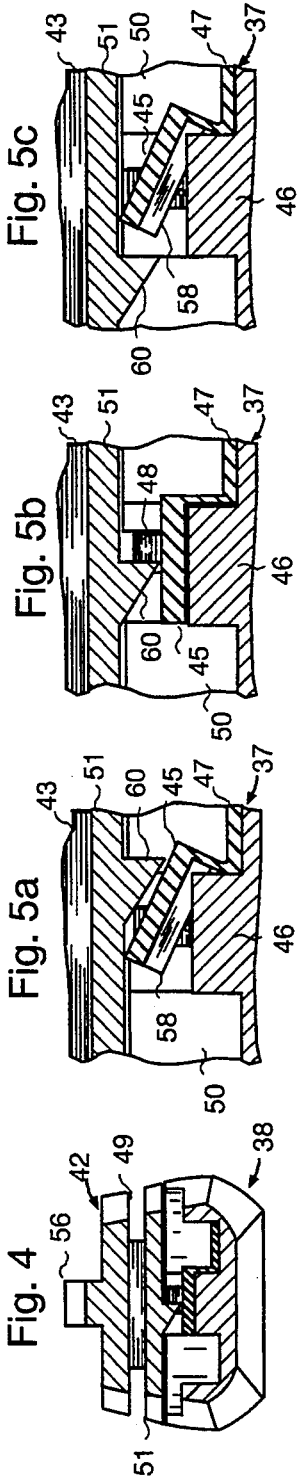
Fig. 3
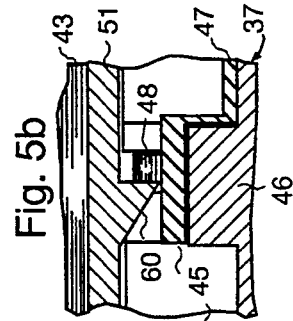
Fig. 5a
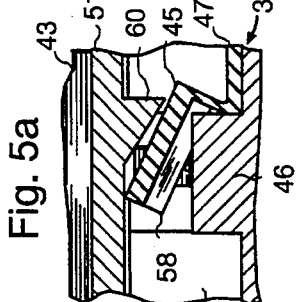
Fig. 5b
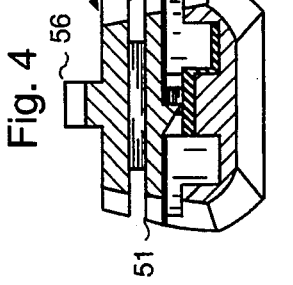
Fig. 5c
Fig. 4

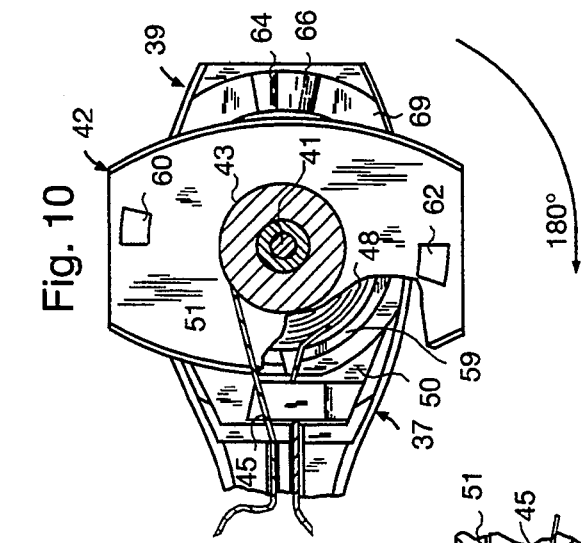
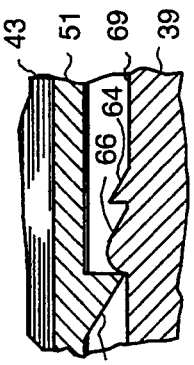
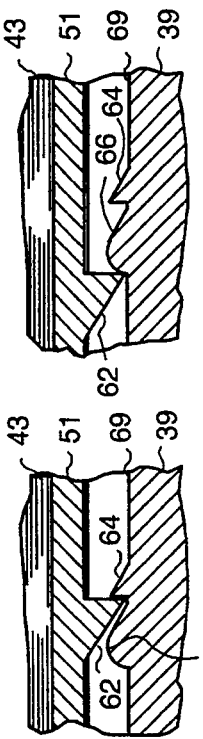
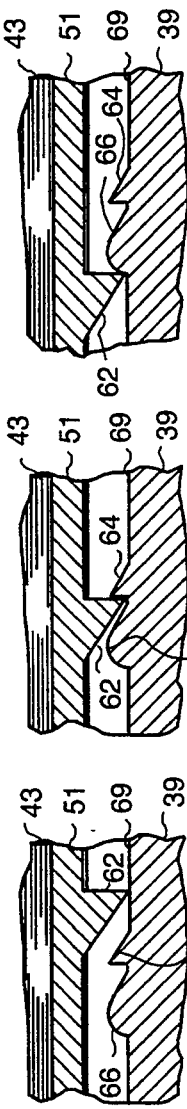
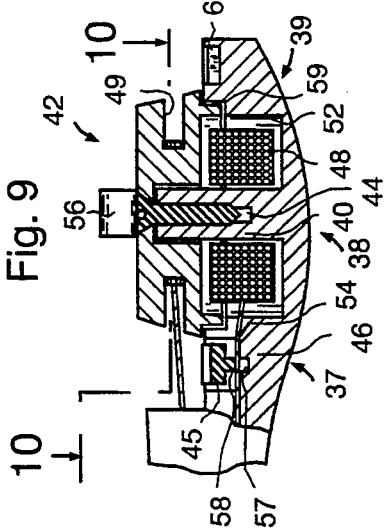
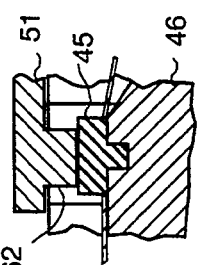
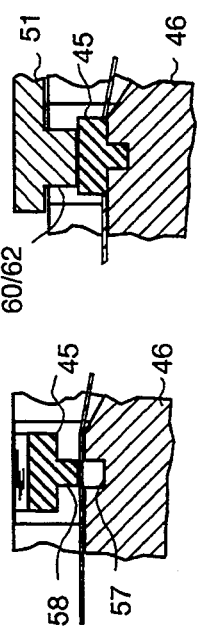
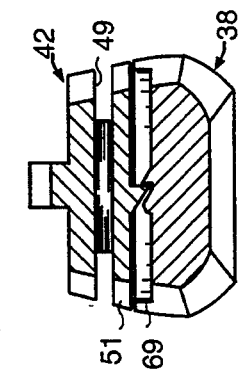
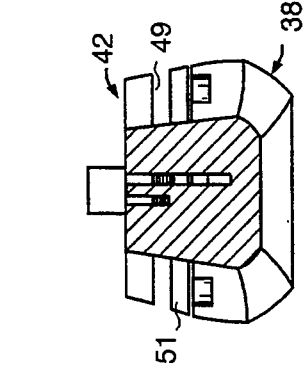

DENTAL FLOSS

FIELD OF THE INVENTION

This invention refers to a dental flossing device; in which the floss is held taut between the teeth of a fork with the help of a lock device and a reeling spool.

BACKGROUND OF THE INVENTION

The dental flossing devices in dental care allow cleaning of the space between teeth. The dental floss is held taut between two teeth of a fork and both ends of the floss are fastened to the device. There is a known dental floss device described in U.S. Pat. No. 4,790,336 in which the floss is guided from a reservoir through a groove and movable clip, wound two times on a tensioning cylinder, advances through the teeth of the fork and through a groove to the take-up cylinder where the floss is wound.

The tension of the floss between the teeth of the fork is achieved through the different diameters of the named cylinders, and an additional movable clip secures the floss.

If the movable clip is not in the lock position, the tautness of the floss is lost and the floss can slide out of the teeth of the fork, The movable clip has to be manually operated.

Since the take-up cylinder is not secured against reverse rotation, any pressure on the floss causes a loss of tension and the floss slides out of the teeth of the fork.

The advantages of the present invention are significantly described as follows: the advancing of the floss and the securing of the tautness of the floss are achieved by turning the reeling spool by 180°.

BRIEF DESCRIPTION OF DRAWINGS

FIG. 1 is a top plan view of the dental flossing device;

FIG. 2 is a side elevation view in section, taken along the line 2—2 of FIG. 1;

FIG. 3 is an enlarged sectional view of FIG. 2 showing a projection on top of the locking tooth;

FIG. 4 is a sectional view of the lock device taken along the line 4—4 of FIG. 1;

FIG. 5a is an enlarged sectional view of the lock device of FIG. 4, showing the lock device in open position;

FIG. 5b is an enlarged sectional view of the lock device of FIG. 4 showing a projection engaging the lock device to clamp a length of floss;

FIG. 5c is an enlarged sectional view of the lock device of FIG. 4, showing the lock device in open position;

FIG. 6 is a sectional view of the locking tooth and stop tooth, taken along the line 6—6 of FIG. 1;

FIG. 7a, 7b, 7c, are enlarged sectional views of the locking tooth and stop tooth of FIG. 6 in 3 different positions;

FIG. 8 is a sectional view of the handle, taken along the line 8—8 of FIG. 1;

FIG. 9 is a partial side view in section, taken along the line 2—2 of FIG. 1 showing the reeling spool turned at 90° angle;

FIG. 10 is a partial top view in section, taken along the line 10—10 of FIG. 9;

FIG. 11 is an enlarged sectional view of the lock device of FIG. 9 showing the lock device in open position;

FIG. 12 is an enlarged sectional view of the lock device of FIG. 2 showing a projection engaging the lock device to clamp a length of floss.

DETAILED DESCRIPTION

The figures show a dental flossing device 10 having a handle 36 with a pair of ends. On one end of the handle is a fork 13 with a pair of teeth 14, 16 each having a cross groove 32, 34 situated at the ends 24, 26 thereof. On the other end of the handle is a floss reservoir 38 with a centrally disposed spindle 40 mounted therein.

The handle 36 further comprises a pair of grooves 20, 22 located on the top side thereof. The pair of grooves extend toward the floss reservoir 38 in a first direction and extend to the teeth 14, 16 of the fork 13 in a second opposite direction.

The floss reservoir 38 has a rounded opening 52, a sealing groove 59 and a freely rotating dental floss spool 48 in it. On one side of the floss reservoir is a lock device 45 resiliently mounted thereon adjacent a first groove 50 formed in the reservoir. The lock device 45 is movable in upward and downward direction. The lock device has a trap 58 which fits in the groove 57. On the opposite side of the reservoir are a locking tooth 64 and a stop tooth 66 mounted in a rounded groove 69. A second groove 54 is located between the rounded opening 52 and the lock device 45.

A reeling spool 42 is rotatably mounted on the spindle 40 and secured with a screw 41 in the bore 44 of the spindle 40. The reeling spool has a top and bottom elliptical shaped dishes 49, 51. The top dish 49 has a turn grip 56 formed thereon. The bottom dish 51 has a pair of oppositely mounted projections 60, 62 and a sealing ring 53 extending therefrom. Between the top and bottom dish is a cylinder 43.

In the present invention, the floss is extended from the floss reservoir 38, through a groove 54 between cross groove 57 and lock device 45, through the groove 20 of the handle 36, through the cross groove 32 of the tooth 14, through the space between the teeth 14, 16 of the fork 13 in the cross groove 34 of the opposite tooth 16, through the groove 22 of the handle 36 and is wound on the cylinder 43 of the reeling spool 42.

In use, one of the projections 60 engages lock device 45, when the reeling spool 42 is rotated to a locking position, to bias lock device 45 downwardly in the first groove 50 thereby allowing lock device 45 to clamp a length of floss. The other projection 62 engages locking tooth 64 and stop tooth 66 when the reeling spool is rotated to the locking position, thereby securing the reeling spool against reverse rotation.

To provide a fresh supply of floss between the teeth 24, 26 of the fork 13, the reeling spool 42 has to be rotated clockwise by 180°.

The rotation of the reeling spool 42 disengages one of the projections 60, the lock device 45 moves upwards, and the floss is pulled. After a rotation of the reeling spool 42 by 180° the reeling spool reaches the lock position, lock device 45 clamps a length of floss and the reeling spool 42 is secured against reverse rotation.

The floss is taut and the dental flosser is ready to use.

What is claimed is:

1. A dental flossing device, comprising:
   a handle having a pair of ends, said handle having a fork mounted at one of said ends and a floss reservoir mounted at the other of said ends, said floss reservoir having a centrally disposed spindle mounted therein;

a reeling spool rotatably mounted upon said spindle, said reeling spool having a top portion and a bottom portion, said bottom portion further having a pair of oppositely mounted projections extending therefrom;

said reservoir further comprising a lock device resiliently mounted thereon adjacent a first groove formed in said reservoir, said lock device being of a size and shape which fits in and mates with said first groove, said lock device movable in upward and downward directions, said reservoir further comprising a locking tooth and a stop tooth mounted opposite said lock device;

wherein one of the said projections engages said lock device when said spool is rotated to a locking position to bias said lock device downwardly in said first groove thereby allowing said lock device to clamp a length of floss;

wherein the other of said projections engages said locking tooth and said stop tooth when said spool is rotated to said locking position.

2. The flossing device of claim 1, further comprising a sealing groove formed in said reservoir, said sealing groove mating with a sealing ring formed on said spool.

3. The flossing device of claim 1, wherein said spindle further comprises a bore which receives a screw therein for securing said spool to said spindle.

4. The flossing device of claim 1, wherein said lock device is mounted by a spring.

5. The flossing device of claim 1, wherein said locking tooth and said stop tooth are mounted in a rounded groove, said rounded groove extending through said reservoir.

6. The flossing device of claim 1, further comprising a length of dental floss carried by said reservoir.

7. The flossing device of claim 1, wherein said fork further comprises a pair of teeth, said teeth each having a cross groove situated in an end thereof.

8. The flossing device of claim 7, wherein said handle further comprises a pair of grooves located on the top side thereof, said pair of grooves extending toward said reservoir in a first direction and extending to said teeth of said fork in a second opposite direction.

9. The flossing device of claim 8, further comprising a second groove located within said reservoir and between said first groove and said lock device.

10. The flossing device of claim 9, further comprising a length of floss carried by said reservoir, said length of floss adapted to be extended through said second groove, said pair of grooves of said handle and said cross grooves of said teeth, and to be wound on said spool.

11. The flossing device of claim 1, wherein said top and bottom portions of said spool further comprises top and bottom elliptical shaped dishes, said top dish having a turn grip formed thereon.

* * * * *